United States Patent [19]
Mark et al.

[11] Patent Number: 5,818,045
[45] Date of Patent: Oct. 6, 1998

[54] SPECTROSCOPIC SYSTEM FOR QUANTIFYING CONSTITUENTS IN NATURAL PRODUCTS

[76] Inventors: Howard L. Mark, 21 Terrace Ave., Suffern, N.Y. 10901; Barry J. Read, 184-3 N. Rte. 303, Congers, N.Y. 10920

[21] Appl. No.: 684,220

[22] Filed: Jul. 19, 1996

[51] Int. Cl.$^6$ ............................ G01N 21/17; G01N 21/25
[52] U.S. Cl. ............................ 250/339.12; 250/339.11; 250/910; 356/418; 356/419
[58] Field of Search ........................ 250/339.07, 339.09, 250/339.11, 339.12, 343, 252.1 A, 910, 341.8; 356/416, 418, 419, 432

[56] References Cited

U.S. PATENT DOCUMENTS

| | | | |
|---|---|---|---|
| 3,776,642 | 12/1973 | Anson et al. | 250/339.11 X |
| 3,828,173 | 8/1974 | Knepler | 250/339.11 X |
| 3,979,589 | 9/1976 | Sternberg et al. | 250/252.1 |
| 4,040,747 | 8/1977 | Webster | 250/339.12 X |
| 4,066,364 | 1/1978 | Emerson | 250/343 X |
| 4,153,837 | 5/1979 | Ross | 250/343 |
| 4,253,766 | 3/1981 | Funk | 250/339.11 X |
| 4,286,327 | 8/1981 | Rosenthal et al. | 250/910 X |
| 4,627,008 | 12/1986 | Rosenthal | 250/910 X |
| 4,883,953 | 11/1989 | Koashi et al. | 250/226 |

OTHER PUBLICATIONS

Product information published by Zeltex, Inc., 130 Western Maryland Parkway, Hagerstown, Maryland 21704.
Michele R. Fischer and Gary M. Hieftje, "Near–IR Multiplex Bandpass Spectrometer Utilizing Polymer Filters," *Applied Spectroscopy*, vol. 50, No. 10, 1996, pp. 1246–1252, no month.

*Primary Examiner*—Edward J. Glick
*Attorney, Agent, or Firm*—St. Onge Steward Johnston & Reens LLC

[57] ABSTRACT

A spectroscopic system for measuring content of a constituent in a sample of a natural product is provided. The spectroscopic system includes a source for electromagnetic (EM) radiation and an absorbance filter for filtering EM radiation received from the source, where the absorbance filter transmits EM radiation of predetermined wavelengths solely by the absorbance characteristics of the filter material. The spectroscopic system also includes a sample holder which is positioned adjacent the source with the absorbance filter positioned therebetween such that only EM radiation of predetermined wavelengths are incident on the sample, a detector for generating an electrical signal indicative of the EM radiation resulting from interaction of the incident EM radiation of predetermined wavelengths with the sample of the natural product and a processing circuit, preferably a microprocessor with memory, responsive to the resulting EM radiation indicative signal for determining the content of the constituent in the sample of the natural product.

22 Claims, 4 Drawing Sheets

SPECTROSCOPIC SYSTEM FOR QUANTIFYING CONSTITUENTS IN NATURAL PRODUCTS

FIELD OF THE INVENTION

The invention relates to a spectroscopic analyzer for measuring contents of constituents in natural products, and more specifically, to a spectroscopic analyzer for measuring contents of constituents in natural products utilizing inexpensive, broad-band filters.

BACKGROUND OF THE INVENTION

Chemical analysis of natural products, such as cereal grains, is an essential aspect of trading in natural products. For cereal grains, the two constituents of greatest interest are protein and moisture. Measuring moisture content of cereal grains is important for two reasons. First, water can be artificially added to increase the weight of a grain, thereby artificially inflating the price. Second, if the water content rises above a certain critical value (e.g., 14% of weight for wheat), then the grain is prone to rotting. Measuring protein content of cereal grains is important because this property determines the suitability for various uses, and consequently, the price. For example, wheat with "high" protein content used for making bread commands a much higher price than wheat with "low" protein content. Note that protein content varies inversely with moisture content; i.e., the more protein (as % of weight) there is, the less moisture there is and vice versa.

The use of near-infrared spectrometers to measure protein and moisture content in natural products is known in the art. In fact, with respect to wheat, this method has become the most popular method for measuring protein and moisture content, and has been approved by the Federal Grain Inspection Service (FGIS).

Chemical analysis via spectrometers is based upon absorbance of electromagnetic (EM) radiation, such as light, by a sample of material (e.g. wheat) when the two interact. Absorbance, as known, is dependent on the thickness of the sample, the concentration of the constituent under consideration and the strength of the interaction between the sample and the EM radiation. Although exceptions exist, visible and ultra-violet radiation interact with electron shells, while infrared and near-infrared radiation interact with vibrations of the nuclei. In any spectral region, the absorbance values of EM radiation at different wavelengths is an intrinsic property of the sample of material in question. This means that the wavelengths of EM radiation that will interact with the sample can be made to depend only upon the chemical composition of the sample.

The most common implementation of spectroscopic instrumentation for quantitative (i.e., determining how much of a given constituent is in a sample) chemical analysis employs the concept of separating and selecting a single desired wavelength at a time from the EM radiation spectrum, allowing the wavelength of EM radiation to interact with the sample and measuring the strength of the interaction between the EM radiation and the sample at this wavelength. From this measurement, the absorbance of the EM radiation by the sample at the wavelength is determined. The absorbance data collected for each selected wavelength is then used to determine the content of the constituent in the sample (by establishing fairly complex mathematical relationships). This concept of separating and selecting a single desired wavelength at a time to determine the content of a specific constituent in a sample is known as the narrow-band method.

How are the desired wavelengths for the narrow-band method separated and selected? One way is to use interference filters. An interference filter is basically a substrate (e.g. glass) that passes through all wavelengths of EM radiation in the spectral region of interest (e.g., visible region), coated with layers of material that alternately have high and low refractive indices. The thicknesses of the layers are carefully controlled so that phases of the EM radiation reflected at the boundaries of the layers cause both constructive and destructive interference, as desired. By allowing only EM radiation of desired wavelength to interfere constructively in the forward direction, EM radiation at only such wavelength will pass through the interference filter.

Some of the other ways of separating and selecting the desired wavelengths for the narrow-band method are: using prisms, diffraction gratings, diode arrays, acousto-optical tuned filters and light emitting diodes (LEDs).

Another widely used implementation of spectroscopic instrumentation for quantitative chemical analysis employs the concept of allowing EM radiation over a wide range of wavelengths to interact with a sample of material contemporaneously. The EM radiation is "encoded" in such a manner that the amount of radiation at each wavelength that interacts with the sample can be determined by mathematical computations. Once the amount of radiation that interacts with the sample at each wavelength is determined, the content of the constituent in question can be calculated. This is known as the broad-band method.

How is EM radiation "encoded" in the broad-band method? One way is by use of an interferometer. This manner of encoding is very common in the infrared portion of the spectrum, and the mathematical process known as Fourier Transform is applied to recover the intensity of the EM radiation at each wavelength.

Another way involves the use of Hadamard matrices to create a scheme for selecting combinations of slits. By utilizing different combinations of slits, the intensity of the EM radiation at each wavelength can be recovered through computations that are essentially the same as solving simultaneous equations.

A third implementation of spectroscopic instrumentation for quantitative chemical analysis, known as the non-dispersive method, utilizes a filter or test cell containing the constituent in the sample to be measured. The presence of the constituent in the filter causes the filter to absorb wavelengths of EM radiation which would otherwise have been absorbed by the sample. After the interaction of the sample with the EM radiation transmitted through the filter is measured, a second measurement is made with a reference cell in place of the filter. The reference cell contains non-absorbing material. The difference in the measurements is then used to determine the content of constituent in the sample. Since the filter or test cell contains the constituent in the sample to be measured, this implementation of spectroscopic instrumentation can only be used for analysis of clear gases and liquids.

At the present time, chemical analysis of natural products using spectrometers is a fairly complex and costly undertaking. A spectroscopic system for measuring contents of constituents in a natural product can cost $20,000 or more. Furthermore, because current spectroscopic systems are designed for a laboratory setting, there is no simple and fast way for someone outside of the laboratory setting (e.g., a farmer on his farm) to conduct a quantitative chemical analysis on a sample of material.

The spectroscopic systems in use today require a fine-tuning of the calibration of the spectroscopic instrumentation prior to use in order to achieve accurate readings. Such fine tuning generally requires either a keypad on the instrumentation or an auxiliary computer connected to the instrumentation. In addition, such fine tuning requires the user to obtain at least ten samples of known composition and to perform computations. Furthermore, the accuracy of the spectroscopic systems is dependent upon manufacturing tolerances; e.g., interference filters used in the narrow-band method to separate and select fixed wavelengths are strongly dependent on the thicknesses of the coated layers of materials.

What is desired, therefore, is a spectroscopic system for measuring contents of constituents in a sample of a natural product, such as wheat, which is affordable, portable, easy and reliable to use by novices, and reasonably accurate.

SUMMARY OF THE INVENTION

Accordingly, it is an object of the invention to provide a spectroscopic system for measuring content of a constituent in a sample of a natural product.

Another object of the invention is to provide a portable spectroscopic system which can be easily and reliably used by novices.

A further object of the invention is to provide a spectroscopic system which is low in cost (relative to current spectroscopic analyzers) and not dependent in a significant way on manufacturing tolerances.

Yet another object of the invention is to provide a spectroscopic system which uses any inexpensive, plastic or glass filter that only transmits electromagnetic (EM) radiation of specific wavelengths determined by the absorbance characteristics of the filter material.

Still another object of the invention is to provide a spectroscopic system which uses a rotatable calibrating dial for fine tuning the system so that the determination of content of a constituent in a sample of a natural product is reasonably accurate.

A further object of the invention is to provide a spectroscopic system which uses a cover and a shield to prevent ambient EM radiation from affecting measurements.

Another object of the invention is to provide a spectroscopic system which uses a reflective member to direct EM radiation from EM radiation source directly to a detector to serve as a reference reading.

These and other objects are achieved by a spectroscopic system for measuring content of a constituent in a sample of a natural product, which includes a source of electromagnetic (EM) radiation and an absorbance filter for filtering EM radiation received from the source, where the absorbance filter transmits EM radiation of predetermined wavelengths solely by the absorbance characteristics of the filter material. The spectroscopic system also includes a sample holder positioned adjacent the source with the absorbance filter positioned therebetween such that only EM radiation of predetermined wavelengths are incident on the sample, a detector for generating an electrical signal indicative of the EM radiation resulting from interaction of the incident EM radiation of predetermined wavelengths with the sample of the natural product and a processing circuit responsive to the resulting EM radiation indicative signal for determining the content of the constituent in the sample of the natural product.

Further aspects of the invention include a wheel with a plurality of apertures upon which is attached the absorbance filter, where the wheel is preferably rotated by a motor. Attached to the periphery of the wheel is a skirt having a cutout so that EM radiation from the source can directly impinge on the detector to serve as a reference reading. A rotary quadrature switch electrically connected to the processing circuit allows for easy fine-tuning of the calibration of the spectroscopic system. Pushbuttons electrically connected to the processing circuit permit selection of the fine-tuning function and constituent in the sample to be measured. A cover attached to the housing and a shield for preventing ambient EM radiation from damaging the detector and introducing errors into measurements.

DETAILED DESCRIPTION OF THE INVENTION

Figure 1:
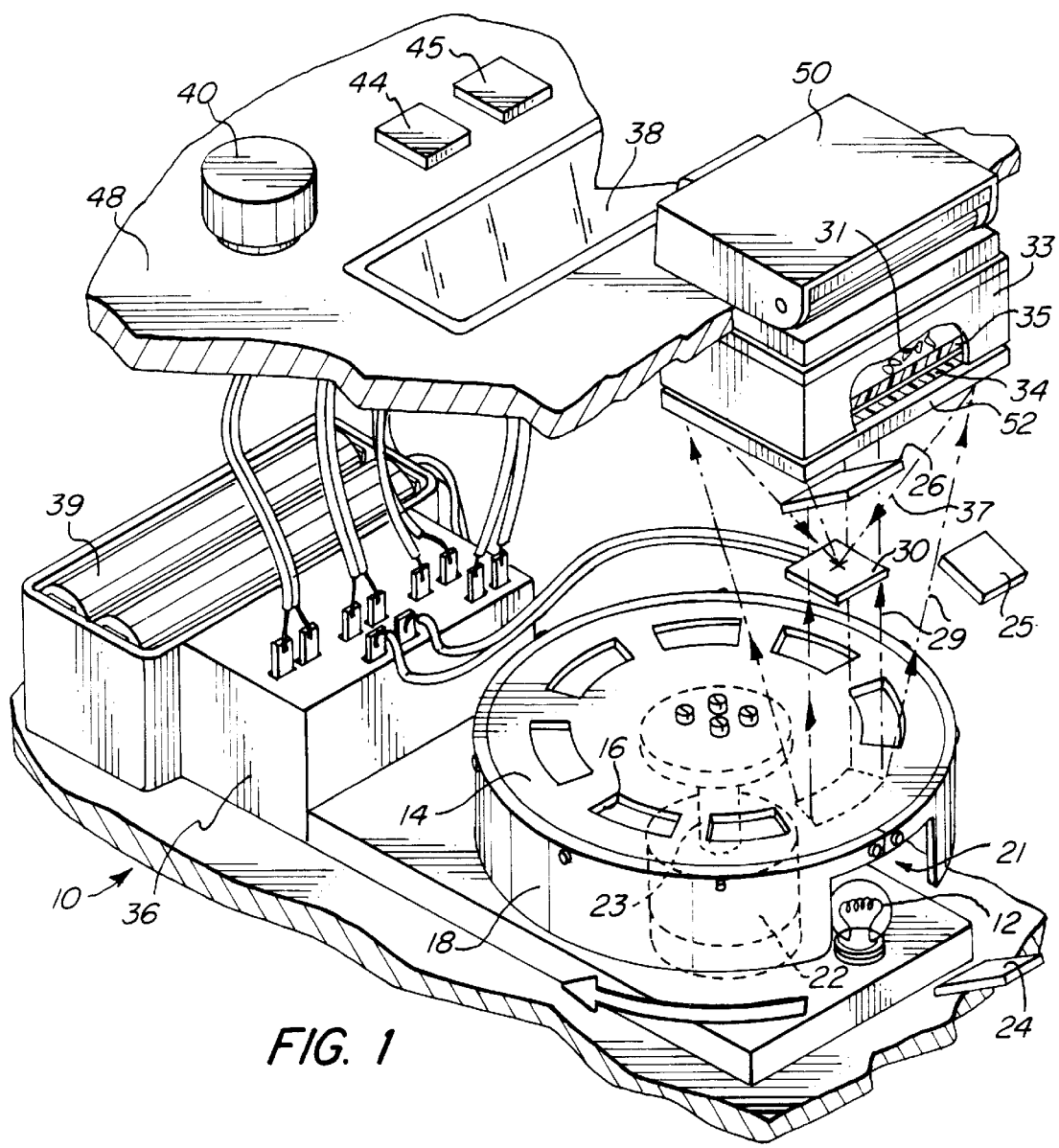
FIG. 1 is an isometric, partially exploded and cutaway view of the spectroscopic system of the present invention.

FIG. 1 is a schematic representation of the spectroscopic system 10 of the present invention. The spectroscopic system 10 includes a source 12 which emits electromagnetic (EM) radiation, a wheel 14 with at least one aperture 16, a skirt 18 attached to the periphery of the wheel 14, an absorbance filter 20 (shown in FIGS. 2 and 3) attached to the wheel 14 below the aperture 16 such that the filter 20 completely covers the aperture 16, a mechanism 22, such as a motor, with a shaft 23 attached to the wheel 14 for rotating the wheel 14, and mirrors 24, 25 and 26. The wheel 14, which need not be circularly configured as shown, is formed from a material which permits no EM radiation to be transmitted therethrough.

The absorbance filter 20, which is preferably made of plastic or glass, is positioned with respect to the source 12 such that EM radiation is received by the filter 20 and only EM radiation of predetermined wavelength or wavelengths are transmitted by the filter 20. The source 12 selected must have a suitable wavelength range so that the predetermined wavelength or wavelengths desired to be transmitted by the filter 20 are encompassed. Although not shown in FIG. 1 (see also FIG. 3), the source 12 may be positioned further from the space defined by the wheel 14 and the skirt 18 so that heat generated by the source 12 is kept away from the filter wheel assembly. In this case, a mirror (not shown) will be positioned within the space defined by the filter wheel assembly such that the EM radiation generated by the source 12 will be reflected by the mirror through reference slit 21 towards mirror 24. The reason for having mirrors 24, 25 and 26 will be discussed hereinbelow.

Also, although not shown in FIG. 1 (shown in FIG. 3), a broadband filter 27 may be positioned between the source 12 and the wheel 14 such that EM radiation of specific wavelengths (e.g., visible and short-wave near infrared radiation) do not impinge on the filter 20. The broadband filter 27 may be necessary if the source 12 emits EM radiation encompassing various undesired wavelengths.

The filter 20, unlike prior art filters, allows only desired wavelengths of EM radiation to be transmitted by the absorbance characteristics of the filter material, which, as discussed above, is preferably plastic or glass. Unlike the prior art non-dispersive method, the filter 20 need not contain the constituent in the sample to be measured. Furthermore, various filtering schemes, such as the interference filter, do not have to be employed for quantitative chemical analysis of natural products.

In the spectroscopic system 10 of the present invention, by selecting the appropriate chemical composition of the absorbance filter 20, the filter 20 will only transmit the desired wavelengths of the EM radiation in accordance with its absorbance characteristics. Selecting the appropriate chemical composition of the absorbance filter 20, including the filter's thickness, is a math intensive procedure which involves testing different chemical compositions to determine their transmission spectra. The mathematics required for this procedure are described hereinafter. Note that since separation and selection of desired wavelengths are no longer significantly dependent upon manufacturing tolerances (chemical composition determines the wavelengths to be transmitted), cost savings and more reliable results are realized.

Selecting the appropriate chemical composition of the absorbance filter 20 requires the following. First, the EM radiation spectrum of the sample must be ascertained. This can be done by employing a known method for chemical analysis using spectrometers (e.g., the narrow-band method). Second, the transmission spectra of the materials (e.g., plastics, glass) being considered for use as filters must be ascertained.

The absorbance of a material is related to the transmission by the following mathematical relationship:

$$A = -\log_{10}(T)$$

where A is the absorbance of a material at a given wavelength and T is the transmission of the material at the given wavelength. Therefore, spectra that are obtained in absorbance may be converted to an equivalent transmission spectra by the inverse logarithmic relationship:

$$T = 10^{-A}.$$

It is preferred that the spectra of the candidate filter materials be corrected for any instrumental effects. One way to do this is to take two spectra for each material: one without the material present in the spectrometer (the "blank" reading) and one with the material in place. The nature of the correction will depend on how the spectrometer reports the results. If the results are reported in absorbance, then the spectral readings from the blank should be subtracted from the spectral readings from the material, wavelength by wavelength. If the spectrometer reports the results in another form (e.g. transmission), then an appropriate mathematical operation can be performed to find an equivalent to the correction used when absorbance is the reporting method of the spectrometer.

Having determined the transmission spectrum of the desired thickness of the filter material, the interaction of the sample with the EM radiation transmitted through the filter is determined by the following mathematical calculations:

1) The spectral readings from the sample must also be converted to equivalent reading for transmittance, reflectance, or other energy-related format.

2) The readings from the sample are multiplied wavelength-by-wavelength by the transmission of the filter at the corresponding wavelengths, to form a set of intermediate terms.

3) Add together the readings representing the transmission of the filter at each wavelength.

4) Add together all the intermediate terms from step 2. Divide this sum by the sum from step 3. This sum represents the total reading that would be obtained by actually measuring the sample through the filter.

These computations can also be expressed by the mathematical equation:

$$R = \Sigma F_i S_i / \Sigma F_i$$

where R represents the computed reading;

$F_i$ represents the transmission of the filter at wavelength i;

$S_i$ represents the transmission (or reflectance, etc.) of the sample at wavelength i; and $\Sigma$ represents the summation operation, over the wavelengths.

Once the transmission spectra of candidate filter materials at different thicknesses have been ascertained, selecting appropriate absorbance filters 20 to measure contents of different constituents is simply a matter of picking the filter or filters that produce the most accurate results using known methods of selection (e.g., testing all possible combinations of available filters).

As shown in FIG. 1, the filter 20, the skirt 18 and the shaft 23 are attached to the wheel 14 by means of screws. However, any attaching means capable of attaching securely can be used. The spectroscopic system 10 further includes a detector 30, a chamber 33 having a first transparent member 34, a removable sample holder 32 with a second transparent member 35 (see FIG. 3) positioned within the chamber 33, a processing circuit 36 electrically connected to the detector 30, and a display screen 38 electrically connected to the processing circuit 36. The sample holder 32, which holds the sample of a natural product such as wheat 31, is positioned with respect to the absorbance filter 20 such that EM radiation of predetermined wavelengths transmitted by the filter 20 (as indicated at 29) are incident on the sample through the first transparent member 34 and the second transparent member 35. In FIG. 1, the detector 30 is shown positioned between the filter 20 and the sample holder 32 to receive and measure EM radiation resulting from interaction of the EM radiation of predetermined wavelengths with the sample 31 (as indicated at 37).

The processing circuit 36, which is preferably a microprocessor with memory, processes the measurements from the detector 30 by applying known mathematical relationships (such as mathematical equations) pre-stored in memory to determine the content of a constituent in the sample of the natural product (for example, protein in wheat). This determination of content of the constituent by the processing circuit 36 is displayed on the screen 38, which may comprise light emitting diodes (LEDs), liquid crystal display (LCD) or cathode ray tube (CRT).

The spectroscopic system 10 of the present invention is preferably portable, although it may just as easily rely upon an external power source. Therefore, the system 10 includes a power source 39, shown in FIG. 1 as batteries, which is coupled the screen 38, the processing circuit 36, the motor 22 and the source 12 of EM radiation. The spectroscopic system 10 also includes a housing 48 which has a cover 50. The cover 50, when closed, prevents ambient EM radiation (such as EM radiation from the sun for outdoor use of the spectroscopic system 10) from entering the spectroscopic system 10. The cover 50 thus protects the detector 30 from possible damage and also ensures that during operation, errors will not be caused due to the presence of ambient EM radiation in the spectroscopic system 10. When the cover 50 is opened (for example to change the sample), there is a shield 52 which will automatically block ambient EM radiation from being incident on the detector 30. The shield 52 automatically moves into place by magnetic or electrical means, such as a motor or a solenoid (not shown) which moves the shield 52 into place by magnetic activation of a switch when the cover 50 is opened. The shield 52 may also move into place by mechanical means, such as a rod connecting the shield 52 and the cover 50.

On the housing 48, there is shown a rotatable calibrating dial 40, a first pushbutton 44 and a second pushbutton 45. The operation of these components will be described hereinbelow.

Figure 2:
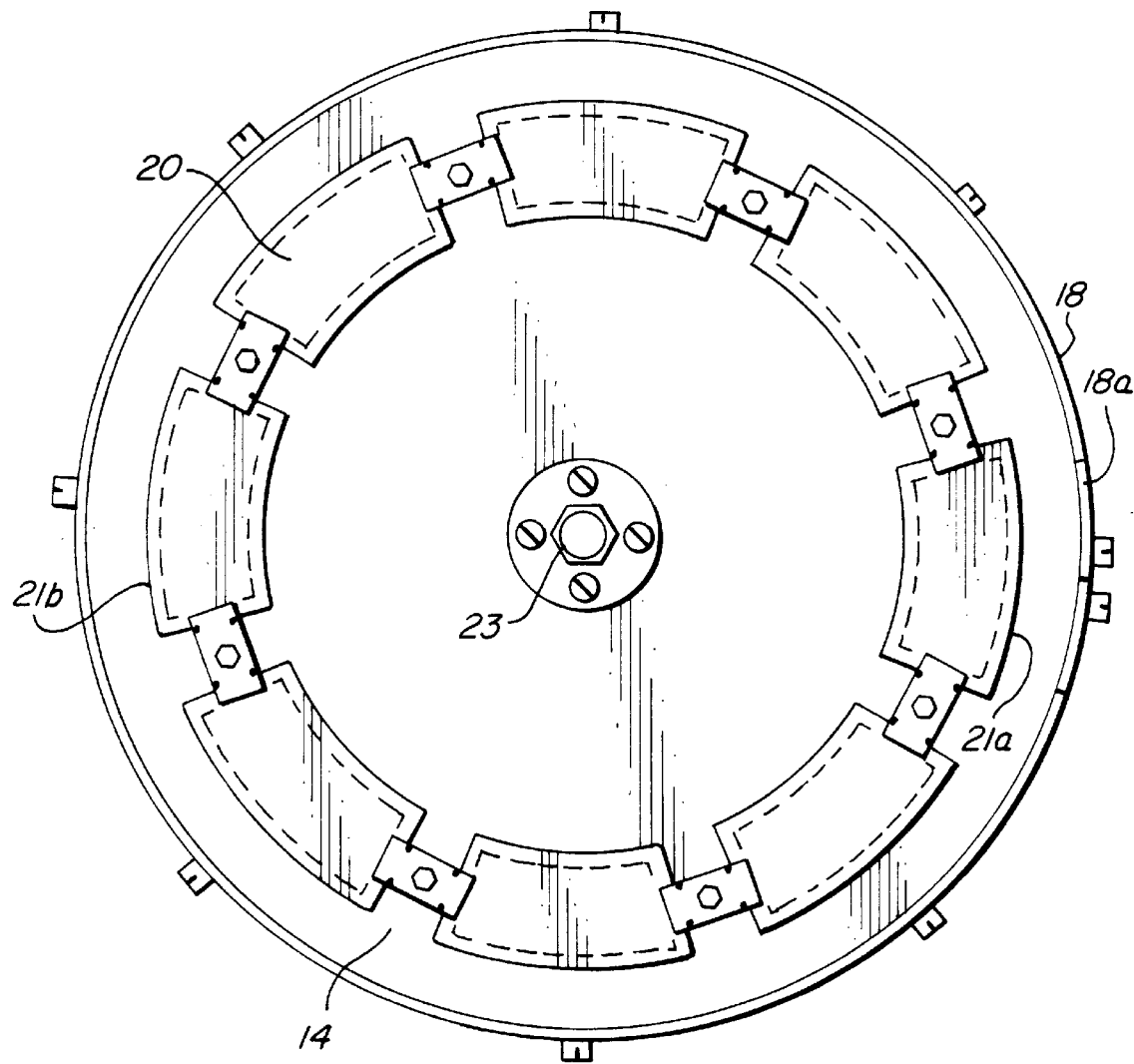
FIG. 2 is a top plan view of the wheel of the spectroscopic system of FIG. 1.

FIG. 2 is a top view of the wheel 14 of the spectroscopic system 10 of FIG. 1. As shown in FIG. 2, there are six absorbance filters 20 attached to the wheel 14 above corresponding apertures 16, and a first blocking "filter" 21a and a second blocking "filter" 21b which allow no EM radiation to be transmitted therethrough. The utilization of six absorbance filters 20 is only for representative purposes. There just needs to be at least one absorbance filter 20 for the spectroscopic system 10 of the present invention to operate properly. The blocking filters 21a and 21b are preferably made from an opaque material such as metal. Note that the blocking filters 21a and 21b would be unnecessary if there are no corresponding apertures 16 on the wheel 14. As is apparent from FIG. 1, the skirt 18 surrounds all but a small portion of the periphery of the wheel 14. The cutout 18a in the skirt 18 is adjacent to the first blocking filter 21a. The reasons for having the cutout 18a and the blocking filters 21a and 21b are to obtain a dark reading and a reference measurement which are used by the processing circuit 36 to more accurately determine content of constituents.

Figure 3:
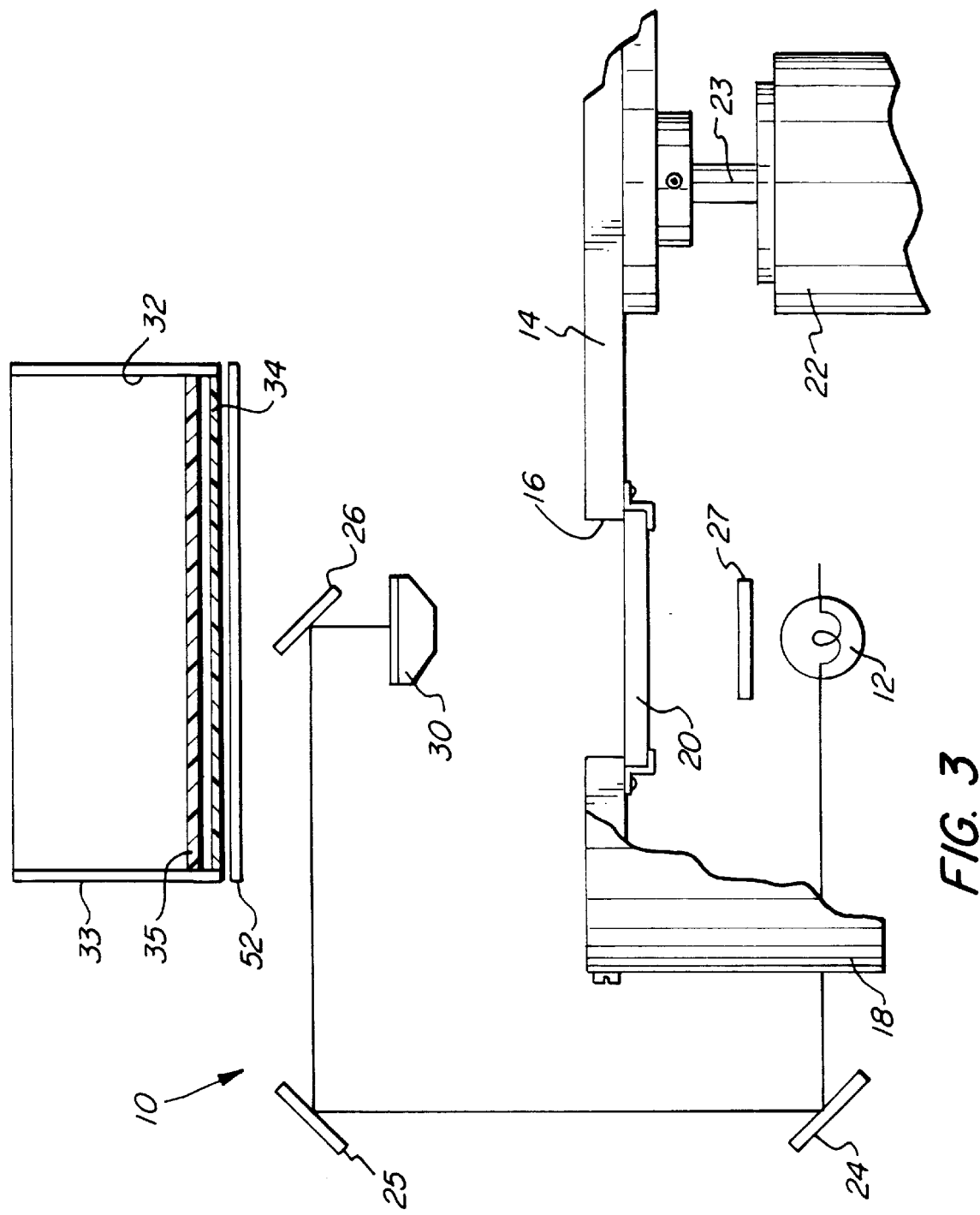
FIG. 3 is a partial enlarged, schematic view of the spectroscopic system of FIG. 1 showing a reference measurement being made.

As the wheel 14 is rotated by the motor 22 via the shaft 23 (note that the wheel 14 may also be rotated by other known mechanical methods or manually), the wheel 14 successively aligns one of the absorbance filters 20 or one of the blocking filters 21a and 21b to receive EM radiation from the source 12. Each absorbance filter 20 is preferably selected to transmit a different set of predetermined wavelengths so that the content of different constituents comprising the sample of the natural product may be measured. When the first blocking filter 21a is positioned to receive EM radiation from the EM radiation source 12, the EM radiation blocked by the first blocking filter 21a passes through the cutout 18a in the skirt 18. This is shown in FIG. 3, which is an enlarged partial side view of FIG. 1. Note that the first blocking filter 21a may be positioned or configured to direct EM radiation reflecting off its surface through the cutout 18a in the skirt 18. The EM radiation which passes through the cutout 18a is directed by the mirrors 24, 25 and 26 to bypass the sample and impinge on the detector 30. Since this EM radiation does not interact with the sample, it serves as a reference measurement for the processing circuit 36.

When the second blocking filter 21b is interposed to receive EM radiation from the EM radiation source 12, no EM radiation is received by the detector 30. This thus serves as a dark (or "zero") reading for the processing circuit 36.

Prior art spectroscopic systems, unlike the present invention, generally require an extra moving part, such as a chopper wheel, to obtain a dark reading. In addition, to obtain a reference reading, prior art spectroscopic systems typically require that a reference material (generally a piece of ceramic that does not absorb radiation) be moved into the path of the EM radiation.

As discussed in the Background of the Invention, prior art spectroscopic systems require additional hardware and complicated procedures to fine-tune the calibration of the spectroscopic instrumentation. In addition to increased cost from the additional hardware, the complicated procedures required by the prior art spectroscopic systems make it very difficult for a novice to use these systems. The present invention makes it easy for a novice to fine-tune the spectroscopic system 10 by employing the rotatable calibrating dial 40, which is preferably a rotary quadrature switch or a potentiometer.

Figure 4:
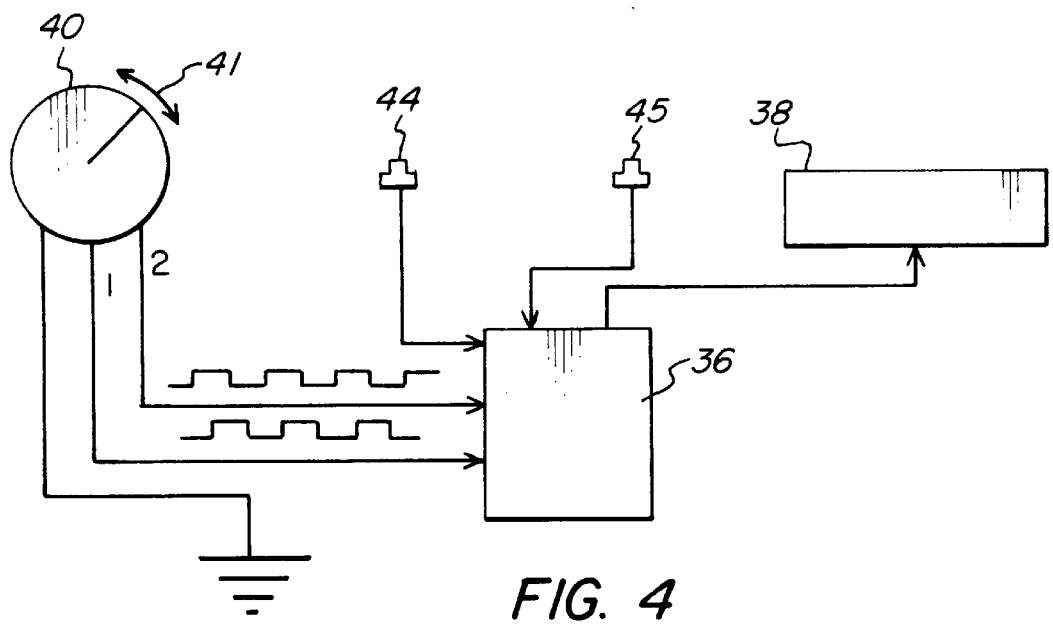
FIG. 4 is an electrical schematic depicting user controls for the spectroscopic system of FIG. 1.
Figure 5:
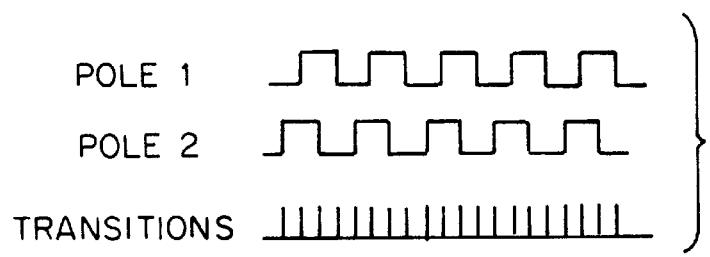
FIG. 5 shows output voltage diagrams for the two poles of the rotary quadrature switch and a diagram indicating each change in the outputs for the two poles.

The fine-tuning of the spectroscopic system 10 is discussed with respect to the rotary quadrature switch illustrated in FIG. 4. The rotary quadrature switch 40 can be rotated in either direction, as indicated by 41. As known, a rotary quadrature switch is a two-pole rotary switch having the frequencies of the two poles out of phase by 90 degrees that opens and closes the contacts alternately, causing the voltage on the output pins to transition from "high" to "low" and vice versa as the switch is rotated. This is shown in FIG. 5. FIG. 5 also shows a graph labeled "TRANSITIONS", with a mark indicating each change from "high" to "low" or vice versa in the poles.

If "clockwise" and "counterclockwise" are used to indicate the two directions of rotation of the rotary quadrature switch 40, then the following conditions are possible at each transition:

| Pole 1 | Pole 2 | Rotation |
|---|---|---|
| Low | Low –> High | Clockwise |
| Low | High –> Low | Counterclockwise |
| High | Low –> High | Counterclockwise |
| High | High –> Low | Clockwise |
| Low –> High | Low | Counterclockwise |
| High –> Low | Low | Clockwise |
| Low –> High | High | Clockwise |
| High –> Low | High | Counterclockwise |

Each transition represents a unique set of conditions. By sensing these transitions, the processing circuit 36 can determine the direction of rotation of the quadrature switch 40. The processing circuit 36 can then determine the proper action to be taken, as described in the following. Note that where a potentiometer is used instead of the quadrature switch 40, an A/D converter would be needed for the processing circuit 36 to determine the changes in resistance.

There are several ways to employ the rotary quadrature switch 40 to fine-tune the calibration of the spectroscopic system 10. Two will be discussed herein for illustrative purposes. First way is to use a single sample which has a known content of a constituent and rotating the rotary quadrature switch 40 until the screen 38 displays the correct value of the content of the constituent in the sample. As the rotary quadrature switch 40 is rotated, the processing circuit 36 senses the transitions discussed above. In response to each transition sensed, the processing circuit 36 adjusts internal constants that are used to calculate the content of constituent in the sample; thus, in this manner, the constants are adjusted (fine-tuned) appropriately.

Second way is to use two samples, one sample containing a known high value of the constituent and the other sample containing a known low value of the constituent. One of the two samples, for example the known low value sample, can be placed in the sample holder 32 and the rotary quadrature switch 40 rotated until the correct value of the constituent is displayed on the screen 38. This will correct the bias. The other sample can then be placed in the sample holder 32 and the rotary quadrature switch 40 rotated until the correct value of the constituent is displayed on the screen 38. This will correct the sensitivity of the spectroscopic system 10. Note that it may be necessary to repeat these adjustments since the second adjustment (for sensitivity) may affect the first adjustment (for bias).

FIG. 4 also shows the first pushbutton 44 and the second pushbutton 45 coupled to the processing circuit 36. The first pushbutton 44 is used to select constituent in a sample to be displayed. For example, where the sample is wheat, the first pushbutton 44 can be used to select between protein and moisture, with one of these (e.g. protein) being the default display selection. More pushbuttons can be employed to accommodate the display of more constituents in a sample. In another embodiment, where a multi-line display screen is used, the first pushbutton 44 would not be needed.

The second pushbutton 45 is used to activate the fine-tuning function of the spectroscopic system 10 of the present invention. The utilization of the second pushbutton 45 thus prevents accidental rotations of the rotary quadrature switch 40 from causing undesired adjustments to the internal constants used to calculate the content of constituent in the sample. Note that although FIG. 4 shows pushbuttons 44 and 45 being used, other types of switches may also be employed, as known in the art.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A spectroscopic system for measuring content of a constituent in a sample of a natural product, comprising:

a source emitting electromagnetic (EM) radiation;

means for individually selecting one of a plurality of broadband absorbance filters, each of said plurality of broadband absorbance filters consisting of a single layer of filter material for filtering EM radiation received from the source, each absorbance filter transmitting EM radiation of predetermined wavelengths solely by the inherent absorbance characteristics of the single layer of filter material;

a sample holder positioned adjacent said source with one of said plurality of absorbance filters therebetween such that only EM radiation of the predetermined wavelengths is incident on the sample;

a detector for generating an electrical signal indicative of EM radiation resulting from interaction of the incident EM radiation of the predetermined wavelengths with the sample of the natural product; and a processing circuit responsive to the resulting EM radiation indicative signal for determining the content of the constituent in the sample of the natural product.

2. The spectroscopic system of claim 1, further comprising a screen for displaying the result of the processing circuit's determination of the constituent content in the sample of the natural product.

3. The spectroscopic system of claim 1, further comprising a shield which prevents ambient EM radiation from being incident on the detector when the system is not in operation.

4. The spectroscopic system of claim 1, further comprising a rotatable calibrating dial coupled to the processing circuit for fine tuning the processing circuit such that the determination of the content of the constituent in the sample of the natural product is made more accurate.

5. The spectroscopic system of claim 1, further comprising a manually actuatable switch for selecting a constituent in the sample of the natural product to be measured.

6. The spectroscopic system of claim 1, further comprising a reflective member for directing the EM radiation from the source directly to the detector such that the measurement for this EM radiation serves as a reference reading for measurement of the EM radiation resulting from interaction of the incident EM radiation of the predetermined wavelengths with the sample of the natural product.

7. The spectroscopic system of claim 1, wherein the filter material is plastic.

8. The spectroscopic system of claim 1, wherein the filter material is glass.

9. A portable spectroscopic system for measuring content of a constituent in a sample of a natural product, comprising:

a housing;

a power supply mounted within said housing;

a source mounted within said housing coupled to said power supply for generating electromagnetic (EM) radiation;

a wheel having openings, said wheel being moveable with respect to said source to bring successive ones of the openings into alignment with said source;

broadband absorbance filters mountable over the openings in said wheel, each broadband absorbance filter comprising a material which receives EM radiation from the source, but only transmits EM radiation of predetermined wavelengths due to the inherent absorbance characteristics of the filter material;

a holder for the sample of the natural product, the holder being positioned such that only EM radiation of the predetermined wavelengths corresponding to a particular opening on the wheel is incident on the sample;

a detector for generating an electrical signal indicative of EM radiation resulting from interaction of the incident EM radiation of the predetermined wavelengths with the sample of the natural product; and a processing circuit responsive to the resulting EM radiation indicative signal for determining the content of the constituent in the sample of the natural product.

10. The portable spectroscopic system of claim 9, further comprising a screen for displaying the result of the processing circuit's determination of the constituent content in the sample of the natural product.

11. The portable spectroscopic system of claim 9, further comprising a shield which prevents ambient EM radiation from being incident on the detector when the system is not in operation.

12. The portable spectroscopic system of claim 9, further comprising a rotatable calibrating dial coupled to the processing circuit for fine tuning the processing circuit such that the determination of the content of the constituent in the sample of the natural product is made more accurate.

13. The portable spectroscopic system of claim 12, wherein the rotatable calibrating dial is a rotary quadrature switch.

14. The portable spectroscopic system of claim 9, further comprising a manually actuatable switch for selecting a constituent in the sample of the natural product to be measured.

15. The portable spectroscopic system of claim 9, further comprising a reflective member for directing the EM radiation from the source directly to the detector such that the measurement for this EM radiation serves as a reference reading for measurement of the EM radiation resulting from interaction of the incident EM radiation of the predetermined wavelengths with the sample of the natural product.

16. The portable spectroscopic system of claim 9, wherein the materials from which the filters are made are plastic.

17. A method of measuring content of a constituent in a sample of a natural product, comprising the steps of:

providing a source of electromagnetic (EM) radiation;

selecting one of a Plurality of broadband absorbance filters each of which transmits EM radiation of predetermined wavelengths solely by the inherent absorbance characteristics of the filter material;

directing EM radiation from said source to said absorbance filter;

positioning the sample of the natural product adjacent said source with said broadband absorbance filter therebetween such that only EM radiation of the predetermined wavelengths is incident on the sample;

detecting with a detector the EM radiation resulting from interaction of the incident EM radiation of the predetermined wavelengths with the sample of the natural product, said detector generating an electrical signal indicative of said resulting EM radiation; and determining the content of the constituent in the sample of the natural product by processing the EM radiation indicative signal.

18. The method of claim 17, further comprising the step of displaying the result of the determination of the constituent content in the sample of the natural product.

19. The method of claim 17, further comprising the step of preventing ambient EM radiation from being incident on said detector.

20. The method of claim 17, further comprising the step of fine tuning the processing of the EM radiation indicative signal by providing a rotatable calibrating dial which is adjusted in accordance with a known content of a constituent in a preselected sample.

21. The method of claim 17, further comprising the step of selecting a constituent in the sample of the natural product to be measured.

22. The method of claim 17, further comprising the step of directing the EM radiation from the source directly to the detector such that the measurement for this EM radiation serves as a reference reading for measurement of the EM radiation resulting from interaction of the incident EM radiation of the predetermined wavelengths with the sample of the natural product.

* * * * *